United States Patent [19]

Wickert

[11] Patent Number: 5,409,838

[45] Date of Patent: Apr. 25, 1995

[54] USE OF ACID TO STABILIZE INDICATOR DYES IN ACRYLATE ADHESIVES

[75] Inventor: Peter D. Wickert, St. Paul, Minn.

[73] Assignee: Minnesota Mining and Manufacturing Company, St. Paul, Minn.

[21] Appl. No.: 247,143

[22] Filed: May 20, 1994

Related U.S. Application Data

[63] Continuation-in-part of Ser. No. 183,060, Jan. 18, 1994, abandoned, which is a continuation-in-part of Ser. No. 995,871, Dec. 23, 1992, abandoned.

[51] Int. Cl.$^6$ ............................................. C12M 1/16
[52] U.S. Cl. ............................................. 436/8; 422/56; 435/299
[58] Field of Search .................. 435/30, 34, 299, 805; 436/8; 422/56-58

[56] References Cited

U.S. PATENT DOCUMENTS

| Re. 24,906 | 12/1960 | Ulrich ........................... 206/59 |
| 3,867,258 | 3/1975 | Forgione ......................... 195/99 |
| 4,476,226 | 10/1984 | Hansen et al. .................. 435/299 |
| 4,565,783 | 1/1986 | Hansen et al. .................. 435/299 |
| 4,895,745 | 1/1990 | Vesley et al. .................... 428/40 |
| 5,089,413 | 2/1992 | Nelson et al. ................... 435/254 |
| 5,232,838 | 8/1993 | Nelson et al. .................... 435/30 |

OTHER PUBLICATIONS

Fred et al., "The Reduction of 2,3,5-Triphenyltetrazolium Chloride by *Penicillium chrysogenum*", *Science*, vol. 109, pp. 169–170, Feb. 18, 1949.

*Primary Examiner*—James C. Housel
*Assistant Examiner*—Rachel Heather Freed
*Attorney, Agent, or Firm*—Gary L. Griswold; Walter N. Kirn; Paul W. Busse

[57] ABSTRACT

The present invention provides a culture device for growing microorganisms having a self supporting substrate coated with a cold-water soluble dry powder which is a mixture of gelling agents and nutrients and a transparent cover sheet having a layer of a water-soluble pressure sensitive adhesive containing indicator dyes on a surface adjacent to the substrate wherein the improvement includes either adding a sufficient amount of a water-insoluble organic acid to the adhesive or including a sufficient amount of acrylic acid as a comonomer in the adhesive in order to inhibit or prevent a premature color change of the indicator dyes.

22 Claims, 1 Drawing Sheet

USE OF ACID TO STABILIZE INDICATOR DYES IN ACRYLATE ADHESIVES

This application is a continuation-in-part application of U.S. patent application Ser. No. 08/183,060, filed Jan. 18, 1994, abandoned which is a continuation-in-part application of U.S. patent application Ser. No. 07/995,871, filed Dec. 23, 1992, abandoned.

The present invention relates to an improved adhesive system for use in a dry culture media system and, more particularly, relates to an acidified water-insoluble adhesive or to an acrylate/acrylic acid water insoluble adhesive capable of stabilizing reduction sensitive indicator dyes which are typically used in such dry culture media systems.

BACKGROUND

A convenient dry culture device for growing microorganisms is described in U.S. Pat. No. 4,565,783 to Hansen et al. In a typical device reported by Hansen et at., a cold-water soluble dry powder containing a gelling agent and microbial growth nutrients is coated on a waterproof substrate. A transparent, read-through cover sheet coated on a surface with an acrylate adhesive containing an indicating dye is attached to the coated substrate. When the device is used, a predetermined amount of an aqueous sample is typically placed in contact with the coated substrate and the cover sheet is placed over the sample and substrate. The aqueous sample hydrates the soluble dry powder which then forms a gelled medium capable of sustaining microbial growth. During the growth period, the indicator dye adhered to the cover sheet reacts in the presence of viable microorganisms to give a detectable response that allows visualization of bacterial colonies which are grown on the culture device. A dry culture device based on the report of Hansen et al. is commercially available as Aerobic Count PETRIFILM plates (Catalog No. 6400, 3M, St. Paul, Minn.).

Another convenient dry culture device for growing aerobic microorganisms such as yeasts and molds is described in U.S. Pat. No. 5,089,413 to Nelson et at. Like the device of Hansen et al., the Nelson et al. device includes a cold-water soluble dry powder containing a gelling agent and microbial growth nutrients coated on a substrate as well as a transparent cover sheet coated with an acrylate adhesive containing an indicating dye. The Nelson et al. device differs from the Hansen et al. device because it contains an additional air permeable membrane layer in order to provide sufficient air or oxygen transmission which is needed for the growth of aerobic organisms such as yeasts and molds. In addition, the nutrients are selected for the growth of yeasts and molds, the indicator dyes are generally specific for yeasts and molds, and antibacterial agents are added to the nutrients in order to prevent contamination of the devices by bacteria or other unwanted microorganisms.

The dry culture devices of both Hansen et al. and Nelson et al. are much simpler to use than conventional gelled agar medium/petri dish systems because there is no need for the user to heat and mix the growth medium, agar and other reagents and then add the mixture to the pour plates. In addition, the devices of Hansen et al. and Nelson et al. are compact and easily disposed of and therefore are easier and safer to use.

In spite of the many advantages that the Hansen et al. or Nelson et al. devices have over conventional types of culture systems, there is a need for increased reagent stability and shelf life in the dry culture devices described above. For example, it has been observed that certain indicator dyes that may be used to aid in the visualization of bacterial colonies grown using the Hansen et al. system tend to be unstable over a period of time in the presence of the other components of the system. See, for example, U.S. Pat. No. 3,867,258 to Forgione that reports that tetrazolium salts used in diagnostic test devices may be stabilized with selected, known antioxidants including alkylated phenols such as butylated hydroxy toluene (BHT), thiobisphenols such as 4,4'-thiobis(6-t-butyl-3-methylphenol) or esters such as distearyl thiodipropionate. In addition, it has been observed that reduction sensitive indicators such as tetrazolium salts, when adhered to thin films with a water-insoluble pressure sensitive adhesive, may inexplicably be reduced to the colored form of the indicator when stored.

Thus, a need exists in the art for a dry culture system which has improved shelf life and enhanced indicator stability compared to current devices.

SUMMARY OF THE INVENTION

It has been determined that the use of indicator dyes in dry culture devices may be particularly sensitive to the adhesives that have been used to adhere the indicator dyes to the surface of the cover sheet of the culture devices. The present invention provides an improved device for growing microorganisms. The improved device has a self-supporting substrate coated with a cold-water soluble dry powder which is a mixture of gelling agents and nutrients and a transparent cover sheet having a surface covered with a layer of a water-insoluble adhesive containing indicator dyes where the adhesive either contains a sufficient amount of a water-insoluble organic acid to inhibit or prevent significant, premature color changes of the indicator dye or the adhesive includes a sufficient amount of acrylic acid, preferably as a comonomer, which also inhibits or prevents premature color changes of the indicator dye.

In general, premature or undesired color changes are readily measured using commercially available instruments which allow measurement of the absolute color of a cover sheet containing an adhesive and indicator dye using the L*a*b* color system defined by the Commission Internationale de l'Eclairage in 1976. Preferably the a* chromaticity value for a cover sheet containing an adhesive and indicator dye remains at a value of less than about +1.20, and more preferably less than about +1.00, over a sufficient period of time. An accelerated aging test may be used to determine the color change of a cover sheet over a period of time. In the aging test, a cover sheet is maintained at a temperature of 120° F. and 90% relative humidity for seven days. After aging for seven days, the a* chromaticity value for a cover sheet containing an adhesive and indicator dye preferably remains at a value of less than about +1.20.

In one preferred embodiment of the invention a copolymeric alkyl acrylate/acrylamide adhesive containing an amount of a $C_8$–$C_{18}$ organic acid is used in a culture device. Suitable organic acids for use in the culture device include acids having a low solubility in water such as caprylic, decanoic, lauric, myristic, palmitic or stearic acid. Stearic acid is a preferred organic acid. The amount of organic acid used in this embodiment of the present invention may be readily determined by those of ordinary skill in the art and is generally about 0.5–2 moles of organic acid for each mole of acrylamide that is in the adhesive used to coat the surface of the cover sheet, i.e., the molar ratio of organic acid to adhesive acrylamide is about 0.5–2:1. In this embodiment of the present invention if the amount of acid added to the adhesive is too high, the pressure sensitive adhesion characteristics of the adhesive are detrimentally effected.

In another preferred embodiment of the invention the adhesive used to adhere the indicator dyes to the transparent cover film is an alkyl acrylate/acrylate acid adhesive prepared with less than about 4 percent by weight, preferably less than about 2 percent by weight of acrylic acid, preferably formulated as a comonomer, to about 96–99 percent by weight of an alkyl acrylate such as isooctyl acrylate in the adhesive, i.e., the weight percent ratio of acrylic acid to isooctyl acrylate in the adhesive is the range of about 1–4:96–99. In this embodiment of the invention, if the amount of acrylic acid added to the adhesive is too high, greater than about 10 weight percent, the adhesive loses its pressure sensitive adhesion characteristics as well as detrimentally affecting the color change of tetrazolium salt indicators. In addition, if the amount of acrylic acid added to the adhesive is about 5–6 weight percent either microbial growth or indication of such growth using known indicators, such as tetrazolium salt indicators, may be detrimentally inhibited as demonstrated in Example 9 below.

In still another embodiment of the invention, methacrylic acid may be used in place of acrylic acid to provide an adhesive formulated as a comonomer of methacrylic acid and an alkyl acrylate.

This invention also includes a process for increasing the stability of an indicator dye adhered to a substrate with a pressure sensitive adhesive that includes contacting the adhesive with a sufficient amount of water-insoluble organic acid or preparing the adhesive with a sufficient amount of acrylic acid comonomer to inhibit or prevent the undesired reduction of the indicator which causes a significant, premature color change of the indicator.

DETAILED DESCRIPTION

Figure 1:
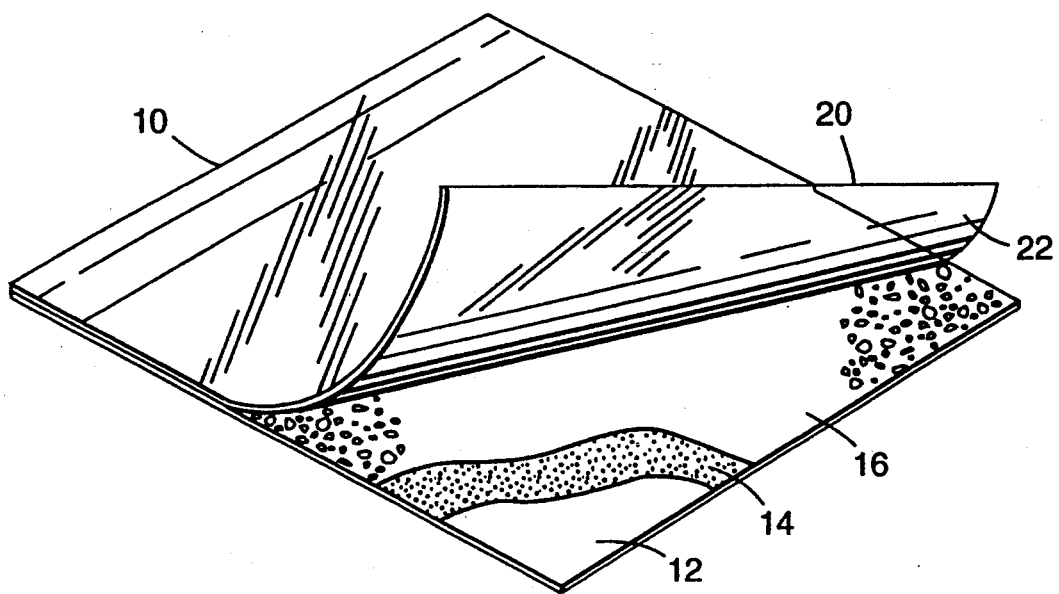
FIG. 1 is a top perspective view, partially in section, of a dry culture device used to grow microorganisms.

The present invention is directed to a dry culture device having an improved adhesive system and is particularly directed to a culture device having an acidified adhesive or having an acrylate/acrylic acid copolymer adhesive which is capable of stabilizing reduction sensitive indicator dyes which are typically used in such dry culture media systems.

FIG. 1 illustrates a culture device suitable for use with the present invention. Such a culture device is described in U.S. Pat. No. 4,565,783 which is incorporated by reference in this application for the purposes of describing the processes of making and using these types of culture devices. Briefly, a dry culture device 10 includes a body member having a self-supporting, waterproof substrate 12. Substrate 12 is preferably a relatively stiff material made of a waterproof material that does not absorb water such as polyester, polypropylene, or polystyrene. Other suitable waterproof materials include substrates such as paper containing a waterproof polyethylene coating.

The upper surface of substrate 12 is coated with a layer of adhesive 14, preferably isooctyl acrylate/acrylamide in a weight ratio of 96/4, which serves to hold a cold-water soluble dry powder 16 that is a mixture of a dry gelling agent and microbial growth nutrients adhered in a uniform layer on the substrate.

The adhesive must be water-insoluble and must not inhibit the growth of the microorganisms. In addition, the adhesive should be sufficiently transparent when hydrated to allow viewing of bacterial colonies growing on the surface of the substrate through the coated substrate. The adhesive 14 should also be coated on the substrate in a thickness which allows the substrate to be uniformly coated with powdered gelling agents and nutrients without completely embedding such particles in the adhesive.

A layer of cold-water soluble dry powder 16 is uniformly adhered to the adhesive layer 14. Preferably, the soluble powder contains gelling agents and microbial growth nutrients. Suitable gelling agents include both natural and synthetic agents which form solutions with water at room temperature. Specific gelling agents include hydroxyethylcellulose, carboxymethyl cellulose, polyacrylamide, locust bean gum, and algin. A preferred gelling agent is guar gum which contains added fumed silica particles to improve the flow of the gum in the dry state. Suitable nutrients for use in the present invention also include nutrients which are soluble in water at room temperature. The specific types of nutrients are selected in order to promote the growth of the microorganisms which will be grown on the substrate 12. A variety of nutrients may be used which include components such as carbohydrates, proteins and minerals. A preferred nutrient mixture includes standard nutrients reported in Standard Methods for the Examination of Dairy Products, 14th Edition, American Public Health Association, Washington, D.C. as well as other salts and minerals such as sodium pyruvate, monobasic potassium phosphate, dibasic potassium phosphate and beef extract.

In the device illustrated in FIG. 1, a cover sheet 20 is attached to one edge of an upper surface of the substrate 12. Cover sheet 20 is preferably made of a transparent film or sheet material in order to facilitate counting of bacterial colonies present on the substrate. In addition, cover sheet 20 is preferably impermeable to bacteria and water vapor in order to avoid the risk of contamination and deterioration of the components. A preferred material for use as a cover sheet 20 is biaxially-oriented polypropylene.

A layer of a water-insoluble adhesive containing an indicator dye is applied on the surface of cover sheet 20 that is adjacent to substrate 12. Suitable adhesives 22 which are applied to cover sheet 20 include acrylate based adhesives such as the adhesives described in U.S. Pat. No. 4,565,783 and U.S. Pat. No. Re 24,906. Preferred adhesives are generally water-insoluble isooctyl acrylate adhesives which will not detrimentally interfere with, or hamper the growth of, microorganisms such as bacteria. If desired, additional gelling agents or nutrients may also be adhered to the adhesive that is applied to the surface of cover sheet 20.

In one preferred embodiment of the invention an alkyl acrylate/acrylamide adhesive which may be used to adhere the cold-water soluble powder to the read-through substrate includes a organic acid which is preferably a $C_8$–$C_{18}$ organic acid or a suitable derivative of such an organic acid. A particularly preferred organic acid is stearic acid. The amount of organic acid used in the present invention may be readily determined by those of ordinary skill in the art and is generally a molar ratio of about 0.5–2 moles of organic acid for each mole of acrylamide in the adhesive which is applied to the surface of cover sheet 20, i.e., the molar ratio of organic acid to adhesive acrylamide is about 0.5–2:1. Amounts of organic acid in excess of about 2 moles of organic acid per mole of acrylamide in the adhesive tend to detrimentally affect the tack of the adhesive or detrimentally affect the pressure sensitive adhesion characteristics of the adhesive.

In another preferred embodiment of the invention the adhesive used to adhere the cold-water soluble powder to cover sheet 20 is an alkyl acrylate/acrylic acid adhesive provided with acrylic acid as a comonomer. The amount of acrylic acid used in the adhesive formulation may be readily determined by those of ordinary skill in the art and the copolymer adhesive preferably is prepared with about 1–4 percent by weight of acrylic acid to about 96–99 percent by weight of isooctyl acrylate in the adhesive. Amounts of acrylic acid in excess of about 5 to 6 weight percent may tend to detrimentally inhibit microbial growth or hinder indication of such growth with suitable indicator dyes.

Suitable indicators dyes for use in the present invention include compounds which are metabolized by the growing organisms and which become colored due to the action of the metabolites produced by developing bacterial colonies. The visual change in color allows for easier detection and visualization of the growing colonies. Preferred indicator dyes include reduction sensitive dyes such as triphenyltetrazolium chloride, p-tolyl tetrazolium red, tetrazolium violet, veratryl tetrazolium blue and related dyes.

Triphenyltetrazolium chloride is a preferred dye for use in devices designed to culture undesired bacteria which may be found in food products such as *S. aureus*, Micrococcus, or other types of bacteria which may be commonly found in food products such as milk or other dairy products.

In use, a predetermined amount of inoculum, typically about one milliliter of inoculum, is added to a device illustrated in FIG. 1 by pulling back cover sheet 20 and adding an aqueous test sample or water to the middle of substrate 12. Cover sheet 20 is then replaced over substrate 12 and the inoculum is evenly spread on the substrate using a weighted circular template which is used to confine the inoculum to a specific area of substrate 12. As the inoculum contacts and is spread on substrate 12, the gelling agents and nutrients adhered to substrate 12 hydrate to form a growth-supporting nutrient gel. The inoculated device is then incubated for a predetermined time after which the number of bacterial colonies growing on the substrate may be counted through the transparent cover sheet 20.

EXAMPLES

The following examples are provided to further illustrate specific embodiments of the present invention. These examples should not be used to limit the scope of the invention which is defined by the appended claims.

Example 1—Comparative Example Using Triphenyltetrazolium Chloride

To an isooctyl acrylate/acrylamide (in a weight ratio of 96/4) pressure sensitive adhesive, as a 21 weight percent solution in ethyl acetate/heptane (in a weight ratio of about 0.48), was added 0.1 weight percent (based on dry adhesive) triphenyltetrazolium chloride (AMRESCO, Solon, Ohio) as a solution in methanol. This adhesive solution was initially colorless. After aging a portion of the solution for seventeen days, the solution was light pink which indicates formation of the red colored formazan from the triphenyltetrazolium chloride (TTC).

The fresh adhesive solution containing TTC, was coated onto a paper with a silicone coating (coating S-8004, H. P. Smith, Chicago, Ill.), at a thickness of about 2 mils. The solvent was removed by drying. Transparent, 1.6 mil biaxially-oriented polypropylene film, corona treated on both sides of the film, was laminated to the adhesive. The adhesive was initially colorless. After seven days of aging, the laminate was viewed through the polypropylene film on a flat black surface with a MINOLTA CR-321 CHROMA METER instrument. This instrument allows measurement of the absolute color of the laminate using the $L^*a^*b^*$ color system defined by the Commission Internationale de l'Eclairage in 1976. After aging for seven days at room temperature, the $a^*$ chromaticity value was $-0.32$. After aging for seven days at 120° F. and 90% relative humidity the $a^*$ value was $+1.84$. For $a^*$ chromaticity values greater than about $+1.20$ it has been observed the top film has a visible pink color. These color measurements indicate a shift of color towards pink (red) caused by a reduction of the TTC which was most pronounced under the extremely stringent higher temperature aging condition.

Aerobic Count PETRIFILM plates (Catalog No. 6400, commercially available from 3M, St. Paul, Minn.) were prepared with cover sheets made from the above polypropylene film with adhesive coating, the coated paper liner being removed. The cover sheets of these PETRIFILM plates, when viewed through the polypropylene with the powdered side down on a flat black surface, with a MINOLTA CR-321 CHROMA METER instrument, gave an average initial $a^*$ value of $+0.61$. After ten days of aging at ambient conditions, the average $a^*$ value was $+0.76$. After ten days of aging at 120° F. at ambient humidity, the average $a^*$ value was $+2.08$.

Example 2—Acrylate/Acrylamide Adhesive and Stearic Acid

To an isooctyl acrylate/acrylamide (in a weight ratio of 96/4) pressure sensitive adhesive, as a 21 weight percent solution in ethyl acetate/heptane (in a weight ratio of about 0.48), was added 0.1 weight percent (based on dry adhesive) TTC (AMRESCO, Solon, Ohio) as a solution in methanol. To three portions of this solution was added stearic acid (Mallinckrodt, Paris, Ky.) at a level of 0.1, 1.0 and 2.0 mole ratio stearic acid to acrylamide. These solutions were initially colorless. After aging the portions of the solutions for seventeen days, the solutions were respectively light pink, colorless, and colorless.

The fresh adhesive solutions were coated onto a paper with a silicone coating (coating S-8004, H. P. Smith, Chicago, Ill.). The solvent was removed by drying. Transparent, 1.6 mil biaxially-oriented polypropylene film, corona treated on both sides of the film, was laminated to the adhesive. The adhesive was initially colorless. After seven days of aging, the laminate was viewed through the polypropylene film on a flat black surface with a MINOLTA CR-321 CHROMA METER instrument. Results of the color measurements are tabulated below.

| Ratio Stearic Acid to Acrylamide | a*, Room Temperature | a*, 120° F. and 90% Relative Humidity |
|---|---|---|
| 0.1 | −0.54 | +0.15 |
| 1.0 | −0.88 | −1.12 |
| 2.0 | −0.88 | −1.25 |

These color measurements indicate that the use of stearic acid in the adhesive inhibits or prevents a shift of color towards pink (red) caused by a reduction of the TTC.

Example 3—Acrylate/Acrylamide Adhesive and Stearic Acid

Aerobic Count PETRIFILM plates (Catalog No. 6400, commercially available from 3M, St. Paul, Minn.) as described in Example 1 were used, except that the cover sheet adhesive contained 0.5 mole ratio stearic acid to acrylamide. The cover sheets, when measured with the MINOLTA CR-321 CHROMA METER instrument had an initial average a* chromaticity value of −0.81. After ten days of aging at room conditions, the average a* value was −0.71. After ten days of aging at 120° F. at ambient humidity, the average a* value was +1.94.

Example 4—Acrylate/Acrylic Acid Adhesive

To an isooctyl acrylate/acrylic acid (in a weight ratio of 98/2) pressure sensitive adhesive, as a 26 weight percent solution in ethyl acetate/heptane (in a weight ratio of about 0.7), was added 0.1 weight percent (based on dry adhesive) TTC (AMRESCO, Solon, Ohio) as a solution in methanol. This adhesive solution was initially colorless. After seventeen days of aging, a portion of the solution was colorless, which indicated no formation of the red colored formazan from the TTC.

The fresh adhesive solution with TTC was coated onto a paper with a silicone coating (coating S-8004, H. P. Smith, Chicago, Ill.), at a thickness of about 2 mils. The solvent was removed by drying. Transparent, 1.6 mil biaxially-oriented polypropylene film, corona treated on both sides of the film, was laminated to the adhesive. The adhesive was initially colorless. After seven days of aging, the laminate was viewed through the polypropylene film on a flat black surface with a MINOLTA CR-321 CHROMA METER instrument. After room temperature aging for seven days the a* chromaticity value was −0.86. After aging at 120° F. and 90% relative humidity for seven days the a* value was −0.97. These color measurements indicated relatively little shift of color towards pink or red color.

Aerobic Count PETRIFILM plates (Catalog No. 6400, commercially available from 3M, St. Paul, Minn.) were prepared as described in Example 1 with use of the above polypropylene film with adhesive coating, the coated paper liner being removed. The cover sheets of the PETRIFILM plates, when viewed through the polypropylene with the powdered side down on a flat black surface, with a MINOLTA CR-321 CHROMA METER instrument, gave an initial average a* chromaticity value of −1.00. After ten days of aging at room conditions, the average a* value was −0.94. After ten days of aging at 120° F. at ambient humidity, the average a* value was −0.47.

To an isooctyl acrylate/acrylic acid (in a weight ratio of 90/10) pressure sensitive adhesive, as a 29 weight percent solution in ethyl acetate/toluene (in a weight ratio of about 2), was added 0.1 weight percent (based on dry adhesive) TTC (AMRESCO, Solon, Ohio) as a solution in methanol. This adhesive solution was initially colorless. After seventeen days of aging, a portion of the solution was colorless, which indicates no formation of the red colored formazan from the TTC.

The fresh adhesive solution with TTC was coated onto a paper with a silicone coating (coating S-8004, H. P. Smith, Chicago, Ill.), at a thickness of about 2 mils. The solvent was removed by drying. Transparent, 1.6 mil biaxially-oriented polypropylene film, corona treated on both sides of the film, was laminated to the adhesive. The adhesive was initially colorless. After seven days of aging, the laminate was viewed through the polypropylene film on a flat black surface with a MINOLTA CR-321 CHROMA METER instrument. After room temperature aging for seven days the a* chromaticity value was −0.91. Ater aging at 120° F. and 90% relative humidity for seven days the a* value was −1.38. These color measurements indicate no significant shift of color towards pink or red color.

Example 5—Acrylate/Acrylamide Adhesive and Octanoic Acid

To an isooctyl acrylate/acrylamide (in a weight ratio of 96/4) pressure sensitive adhesive, as a 21 weight percent solution in ethyl acetate/heptane (in a weight ratio of about 0.48), was added 0.1 weight percent (based on dry adhesive) TTC (AMRESCO, Solon, Ohio) as a solution in methanol. To this solution was added octanoic acid (Aldrich Chemical Co., Milwaukee, Wis.) at a level of 0.5 mole ratio octanoic acid to acrylamide. This solution was initially colorless. After thirteen days of aging, a portion of the solution was also colorless, which indicated no formation of undesired formazan.

Example 6—Comparative Example Using Tetrazolium Violet

To an isooctyl acrylate/acrylamide (in a weight ratio of 96/4) pressure sensitive adhesive, as a 21 weight percent solution in ethyl acetate/heptane (in a weight ratio of about 0.48), was added 0.1 weight percent (based on dry adhesive) tetrazolium violet (Sigma Chemical, St. Louis, Mo.) as a solution in methanol. This adhesive solution was initially light yellow. After twenty days of aging, a portion of the solution was yellow to pink, which indicates formation of the colored formazan from the tetrazolium violet.

The fresh adhesive solution was coated onto a paper with a silicone coating (coating S-8004, H. P. Smith, Chicago, Ill.), at a thickness of about 2 mils. The solvent was removed by drying. Transparent, 1.6 rail biaxially-oriented polypropylene film, corona treated on both sides of the film, was laminated to the adhesive. The adhesive was initially colorless. The laminate was viewed through the polypropylene film on a flat black surface with a MINOLTA CR-321 CHROMA METER instrument. Initially, the a* chromaticity value was −0.88. After seven days of aging at 120° F. and 90% relative humidity, the value was +2.03. This color measurement indicated a shift of color which occurs when tetrazolium violet is reduced.

Example 7—Acrylate/Acrylic Acid Adhesive and Tetrazolium Violet

To an isooctyl acrylate/acrylic acid (in a weight ratio of 98/2) pressure sensitive adhesive, as a 26 weight percent solution in ethyl acetate/heptane (in a weight ratio of about 0.7), was added 0.1 weight percent (based on dry adhesive) tetrazolium violet (Sigma Chemical, St. Louis, Mo.) as a solution in methanol. This adhesive solution was initially light yellow. After twenty days of aging, a portion of the solution was still light yellow, which indicated no formation of the colored formazan from the tetrazolium violet.

The adhesive solution, above, was coated onto a paper with a silicone coating (coating S-8004, H. P. Smith, Chicago, Ill.), at a thickness of about 2 mils. The solvent was removed by drying. Transparent, 1.6 mil biaxially-oriented polypropylene film, corona treated on both sides of the film, was laminated to the adhesive. The adhesive was initially colorless. The laminate was viewed through the polypropylene film on a flat black surface with a MINOLTA CR-321 CHROMA METER instrument. Initially, the $a^*$ chromaticity value was $-0.88$. After seven days of aging at 120° F. and 90% relative humidity, $a^*$ value was $+1.16$. This color measurement indicated relative stability of the tetrazolium violet.

Example 8—Comparative Example Using Antioxidants and Esters

This experiment indicates that stearic acid and distearyl thiodipropionate are not equivalent. Briefly, seven solutions (10 ml of isopropanol and 0.5 ml potassium hydroxide) containing triphenyltetrazolium chloride (about 50 mg)of were prepared. An antioxidant, stearic acid or a mixture of these agents as listed in Table 1, below, was added to six of the solutions. One solution was used as a control. Each of the solutions was maintained at room temperature for one day and then the color of each solution was recorded. The results listed in Table 1 indicate that triphenyltetrazolium chloride may be reduced to the pink colored formazan in the solutions that contained butylated hydroxy toluene, 4,4'-thiobis(6-t-butyl-3-methylphenol), and distearyl thiodipropionate.

Furthermore, the function of stearic acid and distearyl thiodipropionate are very different when triphenyltetrazolium chloride is contacted with the antioxidant 4,4'-thiobis(6-t-butyl-3-methylphenol). Specifically, when triphenyltetrazolium chloride contacted 4,4'-thiobis(6-t-butyl-3-methylphenol) in the presence of stearic acid the indicator did not form the pink colored formazan. In contrast, when triphenyltetrazolium chloride contacted 4,4'-thiobis(6-t-butyl-3-methylphenol) in the presence of distearyl thiodipropionate the indicator was reduced to the pink colored formazan.

TABLE I

| Solution | Color After One Day |
| --- | --- |
| triphenyltetrazolium chloride (ca. 50 mg), isopropanol/methanolic potassium hydroxide* | colorless |
| triphenyltetrazolium chloride (ca. 50 mg), butylated hydroxy toluene (ca. 50 mg), isopropanol/methanolic potassium hydroxide* | Pink |
| triphenyltetrazolium chloride (ca. 50 mg), 4,4'-thiobis(6-t-butyl-3-methylphenol) (ca. 50 mg), isopropanol/methanolic potassium hydroxide* | Pink-Red |
| triphenyltetrazolium chloride (ca. 50 mg), distearyl thiodipropionate (ca. 50 mg), isopropanol/methanolic potassium hydroxide* | colorless |
| triphenyltetrazolium chloride (ca. 50 mg), stearic acid (ca. 50 mg), isopropanol/methanolic potassium hydroxide* | colorless |
| triphenyltetrazolium chloride (ca. 50 mg), 4,4'-thiobis(6-t-butyl-3-methylphenol) (ca. 50 mg), stearic acid (ca. 50 mg), isopropanol/methanolic potassium hydroxide* | colorless |
| triphenyltetrazolium chloride (ca. 50 mg), 4,4'-thiobis(6-t-butyl-3-methylphenol) (ca. 50 mg), distearyl thiodipropionate (ca. 50 mg), isopropanol/methanolic potassium hydroxide* | Pink |

*isopropanol (10 ml)/methanolic potassium hydroxide (0.5 ml)

Another experiment also indicated that distearyl thiodipropionate was not compatible with the water-insoluble pressure sensitive adhesives which were used in the claimed apparatus and methods. Specifically, isooctyl acrylate adhesive was dissolved in solvent (100 ml, isooctyl acrylate/acrylamide adhesive (96/4 weight ratio) as a 21 wt. % solution in ethyl acetate/heptane (0.48 weight ratio)) with both stearic acid (1 g) and distearyl thiodipropionate (1 g). When the adhesive and solvent were combined with stearic acid, a clear solution of the components formed in few minutes after stirring the combination at room temperature. In comparison, when the adhesive and solvent were combined with distearyl thiodipropionate, the combination did not dissolve, mix or combine with the adhesive even when the combination was stirred for an extended period of time at room temperature. This experiment demonstrates that stearic acid and distearyl thiodipropionate were not equivalent and that distearyl thiodipropionate could not be used to make an apparatus which could be used to grow microorganisms. In particular, an acrylate adhesive mixture containing precipitated distearyl thiodipropionate could not be coated onto polymeric substrates or cover sheets which are used to make the now claimed apparatus.

In sum, stearic acid and distearyl thiodipropionate are not equivalent for the purposes of preventing the reduction of tetrazolium salts in the apparatus or methods described in this specification.

Example 9—Comparative Example Using Acrylate/Acrylic Acid Adhesive

Two pressure sensitive adhesive solutions were prepared as follows. Isooctyl acrylate/acrylic acid (176.9 g, in a weight ratio of 90/10) pressure sensitive adhesive, as a 40 weight percent solution in ethyl acetate/toluene (2/1 weight ratio), was mixed with a 1.0 weight percent TTC as a solution in methanol (7.2 ml, AMRESCO, Solon, Ohio). This adhesive solution was initially colorless.

Isooctyl acrylate/acrylic acid (191.6 g, in a weight ratio of 98/2) pressure sensitive adhesive, as a 27 weight percent solution in ethyl acetate/heptane (⅔ weight ratio), was mixed with a 1.0 weight percent TTC as a solution in methanol (5.1 ml, AMRESCO, Solon, Ohio). This adhesive solution was initially colorless.

Both of the above adhesive solutions containing TTC were coated onto a paper with a silicone coating (coating S-8004, H. P. Smith, Chicago, Ill.), at a thickness of about 2 mils. The solvent was removed by drying. Transparent, 1.6 mil biaxially-oriented polypropylene film, corona treated on both sides of the film, was laminated to the adhesive. The laminates were initially colorless.

Using each of the adhesives, essentially similar to Aerobic Count PETRIFILM plates (Catalog No. 6400, commercially available from 3M, St. Paul, Minn.) were prepared as described in Example 1 with use of the above laminated polypropylene film with the coated paper liner being removed.

Two different microbes, *Escherichia coli*, and Pseudomonas sp. were inoculated on each of the different types of plates (2 repetitions) and on two control plates. After incubating at 32° C. for 48 hours all of the plates were read and the observed results are listed in Table II.

In addition, PETRIFILM plates were prepared according to the procedures described in Example 4, with the exception that the isooctyl acrylate/acrylamide (in a weight ratio of 96/4) adhesive on the substrate polyethylene coated paper was replaced with an isooctyl acrylate/acrylic acid adhesive (in a weight ratio of 98/2). These plates were substantially equivalent to plates having 4 weight percent acrylic acid comonomer in the adhesive which is coated on the cover sheet.

Ten different microbes (including Streptococcus sp., Micrococcus sp., *Escherichia coli*, Acinetobacter sp., Pseudomonas sp., Staphylococcus sp., and a diphtheroid) were inoculated on the plates of this example and compared with the plates prepared according to Example 4. On all of the plates, the total number of observed colonies was about the same. However, differences were observed in the color intensity of the indicator dye, triphenyltetrazolium chloride, which was reduced by the inoculated microbes. Lack of color intensity of the indicator suggests that the pH of the growth environment was too acidic to allow the color change of the indicators. With one microbe, the plates prepared in the present example gave more intense colonies compared with the plates prepared according to Example 4. With four microbes, the plates prepared in the present example gave about the same color intensity compared with the plates prepared according to Example 4. With five microbes, the plates of the present example gave less color intensity compared with the plates prepared according to Example 4. Use of lower amounts of acrylic acid comonomer in the adhesive was preferred because the observed color intensity of the indicator was greater and thus allowed for easier identification of microbial colonies.

TABLE II

| ADHESIVE | MICROBE COLONIES DETECTED (COLOR) | |
|---|---|---|
| | E. Coli | Pseudomonas |
| 10% Acrylic Acid: No. 1 (pH 6.35) | 37 (faint color) | 0 (no color) |
| 10% Acrylic Acid: No. 2 (pH 6.23) | 72 (faint color) | 0 (no color) |
| 2% Acrylic Acid: No. 1 (pH 7.78) | 62 (good color) | 7 (excellent color) |
| 2% Acrylic Acid: No. 2 (pH 7.24) | 41 (good color) | 22 (excellent color) |
| Control* No. 1 (pH 7.27) | 54 (excellent color) | 19 (excellent color) |
| Control* No. 2 (pH 7.30) | 70 (excellent color) | 9 (excellent color) |

*Aerobic Count PETRIFILM plates, Catalog No. 6400, 3M, St. Paul, MN

This example shows that a pressure sensitive adhesive containing 10% acrylic acid comonomer is not a suitable adhesive for use in a dry culture medium device. For instance, pseudomonas colonies did not grow at all when this adhesive was used and *E. Coli* colonies grew poorly (compared to the control and a device using a pressure sensitive adhesive containing 2% acrylic acid) when a pressure sensitive adhesive containing 10% acrylic acid comonomer was used. It was surprising that the 2% acrylic acid comonomer pressure sensitive adhesive was dramatically better as an adhesive for use in the dry culture media systems of the present invention. The control plates use 2% acrylic acid comonomer.

The pH of the formulations was measured by adding sterile water to the plate (before inoculation of the plates) and using a surface contact probe available from Beckman Instruments, Inc., Model 39533.

I claim:

1. In a device for growing microorganisms having a self-supporting, waterproof substrate to which is adhered a cold-water soluble powder that includes at least one gelling agent and nutrients and a transparent cover sheet having a layer of an alkyl acrylate/acrylamide adhesive containing an indicator dye applied on a surface of the cover sheet wherein the improvement comprises mixing the adhesive with a sufficient amount of a water-insoluble organic acid to inhibit or prevent substantial, premature color change of the indicator dye.

2. The device of claim 1 wherein the molar ratio of the moles of organic acid to the moles of acrylamide in the adhesive is the range of about 0.5-2:1.

3. The device of claim 1 wherein the molar ratio of the moles of organic acid to the moles of acrylamide in the adhesive is about 0.5:1.

4. The device of claim 1 wherein the organic acid is a $C_8$-$C_{18}$ organic acid.

5. The device of claim 1 wherein the organic acid is stearic acid.

6. In a device for growing microorganisms having a self-supporting, waterproof substrate to which is adhered a cold-water soluble powder that includes at least one gelling agent and nutrients and a transparent cover sheet having a layer of a water-insoluble alkyl acrylate/acrylic acid adhesive containing an indicator dye applied on a surface of the cover sheet wherein the improvement comprises including less than 4 wt. % acrylic acid in the adhesive to inhibit or prevent significant, premature color change of the indicator dye.

7. The device of claim 6 wherein the adhesive comprises less than about 2 wt. % acrylic acid and more than about 98 wt. % of an alkyl acrylate.

8. The device of claim 7 wherein the alkyl acrylate is isooctyl acrylate.

9. A process for increasing the stability of an indicator dye adhered to a substrate with a pressure sensitive alkyl acrylate/acrylamide adhesive comprising the step of mixing the adhesive with a sufficient amount of water-insoluble organic acid to inhibit or prevent undesired reduction of the indicator which causes a premature color change of the indicator.

10. The process of claim 9 wherein the molar ratio of the moles of organic acid to the moles of acrylamide in the adhesive is in the range of about 0.5-2:1.

11. The process of claim 9 wherein the molar ratio of the moles of organic acid to the moles of acrylamide in the adhesive is about 0.5:1.

12. The process of claim 9 wherein the organic acid is a $C_8$-$C_{18}$ organic acid.

13. The process of claim 9 wherein the organic acid is stearic acid.

14. A process for increasing the stability of a reduction-sensitive indicator dye adhered to a substrate with a water-insoluble isooctyl acrylate-based pressure sensitive adhesive comprising the step of copolymerizing isooctyl acrylate with about 4 wt. % acrylic acid to provide a pressure sensitive adhesive which will inhibit or prevent undesired reduction of the indicator which causes a premature color change of the indicator.

15. The process of claim 14 wherein the adhesive comprises about 2 wt. % acrylic acid and about 98 wt. % of an alkyl acrylate.

16. The process of claim 14 wherein the alkyl acrylate is isooctyl acrylate.

17. A device capable of growing microorganisms thereon comprising a cover sheet, a gelling agent, and an alkyl acrylate/acrylamide adhesive containing an indicator dye and a water-insoluble organic acid, wherein the cover sheet has an a* chromaticity value of less than about +1.20.

18. The device of claim 17 wherein the molar ratio of the moles of organic acid to the moles of acrylamide in the adhesive is in the range of about 0.5-2:1.

19. The device of claim 17 wherein the molar ratio of the moles of organic acid to the moles of acrylamide in the adhesive is about 0.5:1.

20. A device capable of growing microorganisms thereon comprising a cover sheet, a gelling agent, a water-insoluble adhesive comprising less than about 4 wt. % acrylic acid and more than about 96 wt. % isooctyl acrylate, and indicator dye, wherein the cover sheet has an a* chromaticity value of less than about +1.20.

21. The device of claim 20 wherein the water-insoluble adhesive comprises about 2 wt. % acrylic acid and 98 wt. % isooctyl acrylate.

22. The device of claim 20 wherein the pH value of the gelling agent and water-insoluble adhesive is greater than about 6.35.

* * * * *